United States Patent [19]
Auchincloss

[11] Patent Number: 4,822,512
[45] Date of Patent: Apr. 18, 1989

[54] BIOCIDAL, PARTICULARLY VIRUCIDAL, COMPOSITIONS

[76] Inventor: Thomas R. Auchincloss, The Grange, Stanningfield, Bury St. Edmunds, Suffolk, England

[21] Appl. No.: 116,711

[22] PCT Filed: Mar. 2, 1987

[86] PCT No.: PCT/GB87/00145
§ 371 Date: Oct. 16, 1987
§ 102(e) Date: Oct. 16, 1987

[87] PCT Pub. No.: WO87/05187
PCT Pub. Date: Sep. 11, 1987

[30] Foreign Application Priority Data

Mar. 1, 1986 [GB] United Kingdom ................. 8605129

[51] Int. Cl.$^4$ ............................................... C11D 3/48
[52] U.S. Cl. ..................................... 252/106; 252/95; 252/99; 252/100; 252/135; 252/142; 252/187.21; 252/187.24; 252/539; 424/130; 424/149
[58] Field of Search .................. 252/95, 99, 100, 106, 252/107, 135, 136, 539, 142, 174.18, 187.21, 187.22, 187.23, 187.24, 187.25; 424/130, 149

[56] References Cited

U.S. PATENT DOCUMENTS 4,104,190  8/1978  Hartshorn ............................. 252/95
4,317,814  3/1982  Laso ..................................... 424/149
4,654,374  3/1987  Martin ................................. 252/106

FOREIGN PATENT DOCUMENTS 188025   7/1986  European Pat. Off. .
932750   7/1963  United Kingdom .
2078522  1/1982  United Kingdom .
2164851  4/1986  United Kingdom .

Primary Examiner—A. Lionel Clingman
Assistant Examiner—Hoa Van Le
Attorney, Agent, or Firm—Neal J. Mosely

[57] ABSTRACT

A dry, water-soluble biocidal composition comprises (a) 0.01 to 5 parts by weight of water-soluble inorganic halide, (b) 25 to 60 parts by weight of an oxidizing agent which, in aqueous solution, reacts with the halide to generate hypohalite ions, (c) 3 to 8 parts by weight of sulfamic acid, (d) 0 to 20 parts by weight of a non-reducing organic acid, (e) 10 to 30 parts by weight of an anhydrous alkali metal phosphate, the parts by weight of the composition totaling 100, the pH of a 1% by weight aqueous solution of the composition being between 1.2 and 5.5, and the composition being characterized by lack of evolution of halogen at a pH less than 3.0 and a biocidal activity substantially greater than that produced by like compositions having inorganic halide concentrations greater than about 20%.

10 Claims, No Drawings

BIOCIDAL, PARTICULARLY VIRUCIDAL, COMPOSITIONS

FIELD OF THE INVENTION

The invention relates to biocidal and specifically virucidal compositions.

Preamble

Hypochlorites in the form of liquid sodium hypochlorite (domestic bleach), or calcium hypochlorite (bleaching powder) and materials such as trichlorocyanuric acid and Chloramine T have been in use for many years as bleaching and sanitising agents for domestic, industrial and to a lesser extent farm use.

These products are marketed as powders and liquids—principally liquids—and have a pH in use ranging from 7 to 11. They all suffer from drawbacks. Liquid products are corrosive, unstable and readily inactivated by organic matter, thus limiting their usefulness and reliability, particularly under farm conditions where large quantitites of organic matter are encountered. Powder products are more stable but are much less reactive. Choramine T for example requires extremely high concentrations to produce an acceptable biocidal effect, and in addition its activity is seriously affected by organic matter.

Because the products are offered in alkaline or neutral formulations their virucidal activity is severely restricted and today in human health and in animal health situations it is recognised that the primary objective of any disinfectant should be to inactivate virus particles, which by and large, are the primary challenge to humans and livestock, resulting ultimately in secondary bacterial infections.

For this purpose the ideal formulations require to be acidic in nature and at an in-use dilution should most preferably give a solution with a pH around 2 to 3. However in simple hypochlorite solutions a pH of 2.3 will liberate chlorine gas from the hypochlorite source and therefore it has not been possible to date to obtain these enhanced virucidal properties.

There is extensive prior art dealing with formulations which set out to achieve stable acidic systems, specifically Du Pont's UK Pat. No. 932 750. Formulations made in accordance with those claimed in the Du Pont patent are however found to be highly unstable in the powder state and to liberate chlorine gas within a short period of manufacture. This is due principally to the use of high concentrations of sulphamic acid and mineral acid salts added to achieve the desired level of acidity. The use of mineral acid boosters to the sulphamic acid, which is there as a chlorine acceptor and stabiliser, besides introducing instability into the formulation also causes the formulation to be highly corrosive. Another disclosure is UK Pat. No. 2 078 522 which seeks to overcome the deficiencies found in the Du Pont patent by using the minimum level of sulphamic acid as a chlorine acceptor and achieving the desired level of acidity at in use dilution by using as a non-reducing acid an organic acid such as malic acid or succinic acid or, alternatively, an acid phosphate salt in combination with the sulphamic acid. This produces a relatively stable powder system which does not liberate chlorine gas when stored for prolonged periods at 37° C., nor does it liberate chlorine as detected by odour and visual examination when the product is dissolved in water at approval dilutions. Chlorine is however liberated if the product is stored in damp conditions or instructions are not followed, and concentrated solutions are made up.

Object of the Invention

The aim of the invention is to improve on known biocidal compositions acting through chlorine/hypochlorite generation, providing a composition with specifically, resistance to chlorine generation not only in the approved dilutions but in conditions in which only a small amount of water is present. Such conditions easily occur in farm use where water may be split on the composition or instructions for making the composition up may not be followed, so that concentrated solutions are generated.

Summary of the Invention

The invention provides a dry, water-soluble biocidal composition comprising:

(a) 0.01 to 5 parts by weight of a water-soluble inorganic halide, (b) 25 to 60 parts by weight of an oxidising agent which, in aqueous solution, reacts with the halide to generate hypohalite ions, (c) 3 to 8 parts by weight of sulphamic acid, (d) 0 to 20 parts by weight of a non-reducing organic acid, (e) 10 to 30 parts by weight of an anhydrous alkali metal phosphate, the pH of a 1% by weight aqueous solution of the composition being between 1.2 and 5.5.

The preferred inorganic halide is sodium chloride with the preferred range from 0.2 to 2 parts by weight when the composition is to be dissolved in the normal domestic water supply.

The problem of chlorine evolution is thus avoided by the use of a low sodium chloride content whilst, at the same time, there is an enhancement of the virucidal activity of the aqueous solution of the composition. This results because of the buffering and chelating effect of the alkali metal phosphate.

The oxidising agent is preferably a persulphate or peroxyphthalate, particularly in the latter case potassium monoperoxy phthalate. The preferred oxidising agent is however the commercially available potassium persulphate triple salt approximately represented by a 2 $KHSO_5 \cdot KHSO_4 \cdot K_2SO_4$ (in weight terms 45:25:30).

Other oxidising agents can be used in amounts equivalent in terms of available oxidising power. The oxidising power of products of this kind is conveniently measured in terms of iodine liberated by reaction with potassium iodide, filtration of the liberated iodine following. The procedure is standard in the art and the results can be expressed in terms of available hypohalite, halogen, or oxygen or simply as "oxidising power".

A non-reducing organic acid is defined as an organic acid that does not reduce the oxidising power of a 1% aqueous solution of a test mixture of 50 parts by weight of the potassium persulphate triple salt referred to above, 45 parts by weight of sodium chloride and 5 parts by weight of sulphamic acid, with the addition of 20 parts by weight of the test acid and left for thirty minutes. The prefered organic acids are malic acid and succinic acid.

Although the preferred inorganic halide is sodium chloride, other halides can be used, for example, potassium chloride, bromide or iodide or sodium bromide or iodide, provided that they do not react with the phosphate to form an insoluble salt.

The alkali metal phosphate may be sodium hexametaphosphate, also known as sodium polyphosphate. Other phosphates, which can be used to replace all or part of the sodium hexametaphosphate, include tetrasodium pyrophosphate, mono-, di- and tri-sodium phosphate, and the corresponding potassium compounds.

The phosphates act as buffering and chelating agents, in combination with the flat pH curve of sulphamic acid, and enable the composition to be effective over a wide range of in-use conditions, for example, the composition can be dissolved in hard water and even in sea water without deleteriously affecting its virucidal properties.

Any surfactant compatible with the acids and oxidising agents can be utilised. A particularly effective surfactant is sodium dodecylbenzene sulphonate. Other suitable surfactants include lauryl ether sulphates, ethylene oxide/propylene oxide aklyl phenol condensates, polyglycol ethers of fatty alcohols, fatty acid ethylene oxide condensates, polyglycol ethers of aklyn phenols, and fatty alcohol ethoxylates. The incorporation of a surfactant in the composition gives the important advantage, particularly at high surfactant levels, of enabling cleaning and disinfecting in a single operation. This is of considerable importance in, for example, the cleaning of poultry houses and other premises in which farm animals are housed.

The composition is preferably made and sold in powder form and made up in water to the required concentration at the point of use, preferably immediately prior to use, though the useful life of the aqueous preparation is significantly longer than that for comparable disinfectant preparations currently available which tend to lose their effectiveness after very few hours. The presence of the phospate in the composition contributes to the extended useful life of the aqueous preparation. The phosphate improves the effectiveness of the composition when dissolved in hard water. The phosphate causes sequestration of any metallic ions which might cause rapid decomposition of the oxidising agents present in the solution.

The aqueous preparation is a broad spectrum virucide and, although the method of viral degradation is not known, it is believed that the lipoprotein cytoplasmic membrane or outer lipid protective layer of the virus is first disrupted thereby exposing the RNA or DNA nucleus of the virus. The sulphamic acid acts as a chlorine acceptor to retain nascent chlorine in solution as an addition product with the sulphamic acid thereby avoiding the evolution of chlorine gas. Maintenance of a low chloride or other halide concentration assists in this prevention of chlorine evolution without in any way reducing the virucidal efficacy of the composition.

Embodiments of the Invention

A virucidal composition was prepared by mixing together the following ingredients:

| | |
|---|---|
| Sodium chloride | 1.5 parts |
| Potassium persulphate triple salt | 50.0 parts |
| Sulphamic Acid | 5.0 parts |
| Malic acid | 10.0 parts |
| Sodium hexametaphosphate | 18.5 parts |
| Sodium dodecylbenzene | 15.0 parts |

The potassium persulphate triple salt has the general formula 2 $KHSO_5 \cdot KHSO_4$ and $K_2SO_4$ and is sold under the name 'Caroat'. It has a minimum active oxygen content of 4.5%. The sodium hexametaphosphate is also known as sodium polyphosphate and is used in powdered or granular form.

The composition was prepared by first mixing together the phosphate and the sulphonate followed by the addition of the persulphate and the acids and, finally, the sodium chloride. A 1% by weight solution of the composition in de-ionised water had a pH of 2.4.

Tests have been carried out to establish the virucidal activity of the above composition in accordance with the standard test procedures of the Ministry of Agriculture, Fisheries and Food of Weybridge, Surrey and of the Animal Virus-Research Institute of Pirbright, Woking, Surrey. These tests have shown the effectiveness of the composition against the following broad spectrum of viruses and viral infections at the dilutions quoted, which gave a 4 log reduction in virus titre.

| Virus Family | Viral Infection | Dilution |
|---|---|---|
| Adenoviridae | Egg Drop Syndrome | 1:100 |
| Herpetoviridae | Infectious Bovine Rhinotracheitis | 1:600 |
| | Aujeszky's Disease | 1:280 |
| | Feline Herpes | 1:200 |
| Iridoviridae | African Swine Fever | 1:200 |
| Parvoviridae | Canine Parvovirus | 1:50 |
| Poxviridae | Pseudo Cowpox | 1:300 |
| Coronaviridae | Transmissible Gastro-Enteritis | 1:450 |
| | Avian Infectious Bronchitis | 1:280 |
| | Canine Coronavirus | 1:100 |
| Orthomyxoviridae | Avian Influenza | 1:320 |
| Paramyxoviridae | Newcastle Disease | 1:280 |
| | Distemper | 1:280 |
| Picornaviridae | Swine Vesicular Disease | 1:200 |
| | Foot & Mouth Disease | 1:1300 |
| Reoviridae | Gumboro (IBD) | 1:250 |
| Retroviridae | Maedi & Visna | 1:400 |
| | AIDS | 1:200 |
| Rhabdoviridae | Rabies | 1:280 |
| Togaviridae | Equine Arteritis | 1:350 |

An important advantage of the disinfectant composition is thus its very broad spectrum of virucidal activity. In addition, as compared to previous disinfectant compositions which have been effective in respect of selected viral infections, the composition of the present invention can be used at higher dilutions and is thus more cost-effective.

For example, comparative results between the composition of the present invention and that given as Example 3 of British Patent Specification No. 2 078 522A give the following Ministry of Agriculture, Fisheries and Food (MAFF) approval levels in respect of Foot and Mouth Virus (F & M), Swine Vesicular Disease Virus (SDV), Fowl Pest Virus (FP) and General Orders (GO) of the MAFF tests against *Salmonella choleraesuis*.

| | Example 3 | This Invention |
|---|---|---|
| F & M | 1:1000 | 1:1300 |
| SVD | 1:80 | 1:200 |
| FP | 1:160 | 1:250 |
| GO | 1:90 | 1:120 |

Tests have been carried out to assess the short term and the long term stability of the dry mixed composition. In the first test a sample was stored at 37° C. in a sealed container and sampled periodically as set out below:

| Time (days) | Oxidising Power Expressed as % Available Chlorine |
|---|---|
| 0 | 10.42 |
| 2 | 10.38 |
| 4 | 10.44 |
| 7 | 10.37 |
| 14 | 10.45 |
| 21 | 10.50 |
| 28 | 10.41 |

The variations in the percentage available chlorine are within the range of anticipated experimental area and indicate excellent short-term stability.

A further sample was then produced and two batches were stored at 20° C. and 37° C. respectively. Results for percentage available chlorine were obtained as follows:

| | Oxidising Power as % Available Chlorine | |
|---|---|---|
| Time (weeks) | 20° C. | 37° C. |
| 0 | 10.14 | — |
| 1 | 10.10 | 10.13 |
| 2 | 10.10 | 10.11 |
| 3 | 10.12 | 10.13 |
| 4 | 10.10 | 10.10 |
| 8 | 10.06 | 10.07 |
| 12 | 10.02 | 10.04 |
| 16 | 10.02 | 10.06 |
| 20 | 10.00 | 10.04 |
| 24 | 10.02 | 10.04 |
| 26 | 9.98 | 10.00 |

In vitro short term exposure trials have been carried out simulating farm conditions in respect of the following bacteria and the bacteriological count results after the specified exposure times were as follows:

| | 5 mins | 15 mins | 30 mins |
|---|---|---|---|
| E. Coli (NCIB 9517) | 13 | 0 | 0 |
| Staph. Aureus (NCIB 9518) | 15 | 0 | 0 |
| Bacillus Cereus (NCIB 10024) | 5 | 0 | 0 |
| Pseudomonas Aeruginosa (NCIB 10421) | 0 | 0 | 0 |

The numbers indicated refer to the number of surviving organisms after the specified exposure periods.

Tests have also been carried out using the material described above at a dilution of 1:400 for the removal of mould species from chicken hatchery material. The material was found to be totally effective in respect of the mould species which were tested, namely *A. flavus*, a Penicillium sp. and Scopulariopsis sp.

Test have also been carried out involving the addition of a 0.5% by weight solution of the composition to the drinking water of poultry. The weights of the birds after one week and at the commencement of the test were carried out and a comparison made with a control group whose drinking water did not contain any additive.

| | Weight at Commencement | Weight after one week |
|---|---|---|
| Test Group | 1738 gms | 1920 gms |
| Control Group | 1730 gms | 1910 gms |

Tests were also carried out in respect of day-old chicks, again using a 0.5% by weight solution and comparing a test group of chicks with a control group.

| | Weight at Commencement | Weight after seven days |
|---|---|---|
| Test Group | 40 gms | 120 gms |
| Control Group | 40 gms | 124 gms |

Tests were also carried out on the effect of spraying a 0.5% by weight solution of the composition in livestock buildings, the tests involving broiler poultry, sows and new-born piglets, calves and horses. Clinical examination of the skin and mucous membranes of the livestock was carried out before and after spraying daily for an extended period, and it was established that there was no inflammatory or any other adverse response on the part of the animals. At the same time, significant benefits were obtained in terms of growth and overall food conversion efficiency.

Additional tests have been carried out comparing the effect of using different phosphates. In each instance, a composition was prepared containing 18.5% by weight of the phosphate and a % by weight aqueous solution of the composition was then prepared. In Test A, the composition was dissolved in de-ionised water, in Test B the composition was dissolved in tap water, and in Test C the composition was dissolved in sea water. The pH of each solution was then measured.

| Phosphate | pH Test A | pH Test B | pH Test C |
|---|---|---|---|
| Tetrasodium diphosphate | 3.0 | 4.1 | 3.0 |
| Monosodium phosphate | 2.5 | 2.5 | 2.4 |
| Disodium phosphate | 3.3 | 3.6 | 3.7 |
| Trisodium phosphate | 3.0 | 5.3 | 4.4 |
| Sodium hexametaphosphate | 2.4 | 3.9 | 3.0 |

No chlorine smell was obtained in respect of the solutions made using de-ionised water though a slight smell was detected using monosodium phosphate in tap water and slight or very slight smells with each of the phosphates when using sea water.

Tests were also carried out to investigate the effect of adding additional malic acid and sulphamic acid to the aqueous solution of the composition prepared as described above, i.e. using sodium hexametaphosphate. In each case a 10% by weight acid solution was prepared and added to a 1% by weight solution of the composition. With the addition of sulphamic acid a pH of 1.2 was eventually reached but, even at this pH, there was no noticeable chlorine odour. With malic acid a pH of 1.8 was eventually reached, again with no noticeable chlorine odour.

Tests have also been carried out to assess the effect of replacing the malic acid by succinic acid. Solutions were prepared by mixing the dry powder ingredients together in the manner described above, and then dissolving 1 part of the mixture in 100 parts of water. Both the malic and succinic acid solutions functioned in exactly the same way. The only detectable difference was that the pH of the malic acid solution was 2.6 whereas that of the succinic acid solution was 2.5.

Dry powder mixes have been prepared by mixing together the following:

| | |
|---|---|
| Potassium Persulphate | 50 parts by weight |
| Sulphamic Acid | 5 parts by weight |
| Malic Acid | 10 parts by weight |
| Sodium Dodecylbenzene sulphonate | 15 parts by weight |
| Sodium chloride and | 20 parts by weight |
| Sodium Hexametaphosphate | |

Samples were then prepared utilising different proportions of sodium chloride and sodium hexametaphosphate to determine the effect of sodium chloride content on chlorine evolution. A paste was prepared comprising 20 gms of the mixture and 5 mls water and 20% by weight aqueous solutions of the mixture were prepared. The test results were as follows:

| Parts Na Cl | Paste Overnight | Paste after 30 mins | 20% Solution Overnight | 20% Solution after 30 mins |
|---|---|---|---|---|
| 5 | + | + | + | − |
| 4 | + | + | + | − |
| 3 | + | + | + | − |
| 2.5 | − | ± | + | − |
| 2 | − | − | − | − |
| 1.5 | − | − | − | − |
| 1 | − | − | − | − |

+ = slight chlorine evolution
± = very slight chlorine evolution
− = no chlorine evolution Even in the very severe test of making up as a paste to simulate wetting of the solid produce, a mixture containing 2.5% by weight of sodium chloride showed only marginal chlorine evolution indicating its total safety for farm use.

The outstanding virucidal activity of the composition according to the invention, together with its bactericidal and fungicidal activity, has been obtained with a composition which is inherently safe to use.

The use of an edible organic acid, e.g. malic acid, to achieve a low pH enables the following benefits to be obtained:
(a) the composition is non-corrosive,
(b) textiles are not bleached,
(c) chickens can drink the aqueous preparation,
(d) the aqueous preparation is not a skin or eye irritant,
(e) there is no chlorine evolution in the specified use conditions,
(f) it is possible to bathe in the aqueous preparation,
(g) the aqueous preparation can be sprayed in occupied rooms without causing discomfort, and
(h) the composition is non-tainting and non-staining.

In use, the mode of operation of the composition is complex. The amino acids in the outer protective layers of enveloped viruses react under acid conditions as quaternary active agents and will coprecipitate with the dodecylbenzene sulphonate or other anionic surfactant. The lipid in the outer envelope will also be solubilised by the surfactant. In addition, the various organic constituents of the viruses, e.g. amino acids, polypeptides, and nuclear DNA or RNA will be oxidised at low pH either by nascent oxygen or by hypochlorous acid generated under the low pH conditions.

I claim:

1. A dry, water-soluble biocidal composition comprising:
   (a) 0.01 to 5 parts by weight of water-soluble inorganic halide,
   (b) 25 to 60 parts by weight of an oxidizing agent which, in aqueous solution, reacts with the halide to generate hypohalite ions,
   (c) 3 to 8 parts by weight of sulfamic acid,
   (d) 0 to 20 parts by weight of a non-reducing organic acid,
   (e) 10 to 30 parts by weight of an anhydrous alkali metal phosphate,
   the parts by weight of the composition totaling 100,
   the pH of a 1% by weight aqueous solution of the composition being between 1.2 and 5.5, and
   said composition being characterized by lack of evolution of halogen at a pH less than 3.0 and a biocidal activity substantially greater than that produced by like compositions having inorganic halide concentrations greater than about 20%.

2. A composition according to claim 1, wherein the inorganic halide is sodium chloride and comprises 0.2 to 2 parts by weight.

3. A composition according to claim 1, wherein the non-reducing organic acid is selected from malic acid and succinic acid, and comprises at least 7 parts by weight.

4. A composition according to claim 1, wherein the alkali metal phosphate is sodium hexamethylphosphate.

5. A composition according to claim 1, wherein the alkali metal phosphate is selected from the group comprising tetrasodium pyrophosphate, mono-, di- and trisodium phosphate and the corresponding potassium compounds.

6. A composition according to claim 1, which additionally includes up to 20 parts by weight of an anhydrous surfactant and in which the composition is prepared by first mixing the alkali metal phosphate and the surfactant.

7. A dry, water-slouble biocidal composition comprising:
   (a) 1.5 parts by weight of sodium chloride,
   (b) 50 parts by weight of potassium persulfate triple salt,
   (c) 10 parts by weight of sulfamic acid,
   (d) 5 parts by weight of malic or succinic acid,
   (e) 18.5 parts by weight of sodium polyphosphate, and metal phosphate,
   (f) 15 parts by weight of sodium dodecylbenzene sulfonate,
   the parts by weight of the composition totaling 100,
   the pH of a 1% by weight aqueous solution of the composition being about 2.4, and
   said composition being characterized by lack of evolution of halogen at a pH of 2.4 and a biocidal activity substantially greater than that produced by like compositions having sodium chloride concentrations greater than about 20%.

8. A broad-range disinfectant and detergent preparation comprising a dilute aqueous solution of a biocidally-active amount of the composition claimed in claim 7.

9. A method of cleaning and disinfecting which comprises applying the disinfectant and detergent solution claimed in claim 8 to a surface or object requiring disinfection.

10. A broad-range biocidal disinfectant and detergent preparation comprising an aqueous solution of the composition claimed in claim 1,
the pH of a 1% by weight aqueous solution of the composition being between 1.2 and 5.5,
said composition being characterized by lack of evolution of halogen at a pH less than 3.0 and a biocidal activity substantially greater than that produced by like compositions having inorganic halide concentrations greater than about 20%.

* * * * *